(12) United States Patent
Meilinger

(10) Patent No.: US 10,041,729 B2
(45) Date of Patent: Aug. 7, 2018

(54) METHOD FOR THE CRYOGENIC FRACTIONATION OF AIR AND AIR FRACTIONATION PLANT

(71) Applicant: LINDE AKTIENGESELLSCHAFT, Munich (DE)

(72) Inventor: Matthias Meilinger, Wolfratshausen (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 240 days.

(21) Appl. No.: 14/828,568

(22) Filed: Aug. 18, 2015

(65) Prior Publication Data

US 2016/0061520 A1 Mar. 3, 2016

(30) Foreign Application Priority Data

Sep. 2, 2014 (EP) .................................. 14003025.5

(51) Int. Cl.
*F25J 3/00* (2006.01)
*F25J 3/04* (2006.01)
(Continued)

(52) U.S. Cl.
CPC ......... *F25J 3/04412* (2013.01); *F25J 3/0486* (2013.01); *F25J 3/04296* (2013.01); *F25J 3/04642* (2013.01); *F25J 3/04654* (2013.01); *F25J 3/04666* (2013.01); *F25J 3/04678* (2013.01); *F25J 3/04709* (2013.01);
(Continued)

(58) Field of Classification Search
CPC .. F25J 3/04412; F25J 3/04745; F25J 3/04751; F25J 3/04757; F25J 3/04642; F25J 3/04654; F25J 3/0466; F25J 3/04666; F25J 3/04709; F25J 3/04739; F25J 3/0486; G01N 1/10; G01N 1/22; G01N 1/2247; G01N 1/2273; G01N 2030/122; G01N 33/0004; G01N 33/0006; G01N 33/0036

See application file for complete search history.

(56) References Cited

U.S. PATENT DOCUMENTS 5,161,381 A * 11/1992 Victor ..................... G01N 1/22
62/50.1
5,629,208 A * 5/1997 Darredeau ........... F25J 3/04412
422/67

(Continued)

FOREIGN PATENT DOCUMENTS

EP 2163878 A1 * 3/2010 ............... G01N 1/10
EP 2163878 A1 3/2010

*Primary Examiner* — Keith Raymond
(74) *Attorney, Agent, or Firm* — Millen White Zelano & Branigan, PC

(57) ABSTRACT

A method for the cryogenic fractionation of air, in which a liquid volume present in a vaporization chamber in a distillation column system of an air fractionation plant is fed by means of a cryogenic liquid and in which a proportion of the liquid volume is continuously transferred into the gas phase by vaporization, wherein, in addition to oxygen, the cryogenic liquid contains components, including xenon, which are higher-boiling than oxygen. The content of xenon in the cryogenic liquid is determined and used as a measure of any enrichment of the components which are higher-boiling than oxygen in the cryogenic liquid. A corresponding air fractionation plant is also described.

19 Claims, 1 Drawing Sheet

(51) Int. Cl.
    *G01N 1/22*         (2006.01)
    *G01N 33/00*       (2006.01)
    *G01N 30/12*       (2006.01)

(52) U.S. Cl.
    CPC ....... *F25J 3/04727* (2013.01); *F25J 3/04745* (2013.01); *F25J 3/04751* (2013.01); *F25J 3/04757* (2013.01); *G01N 1/22* (2013.01); *G01N 1/2247* (2013.01); *G01N 1/2273* (2013.01); *G01N 33/0036* (2013.01); *F25J 2280/02* (2013.01); *G01N 33/0004* (2013.01); *G01N 33/0006* (2013.01); *G01N 2030/122* (2013.01)

(56) References Cited

U.S. PATENT DOCUMENTS

| | | | |
|---|---|---|---|
| 9,341,606 B2 * | 5/2016 | Coleman | G01N 33/0011 |
| 2006/0107831 A1 * | 5/2006 | Karwacki, Jr. | B01D 53/04 |
| | | | 95/116 |
| 2010/0037656 A1 * | 2/2010 | Prosser | F25J 3/0409 |
| | | | 62/643 |

* cited by examiner

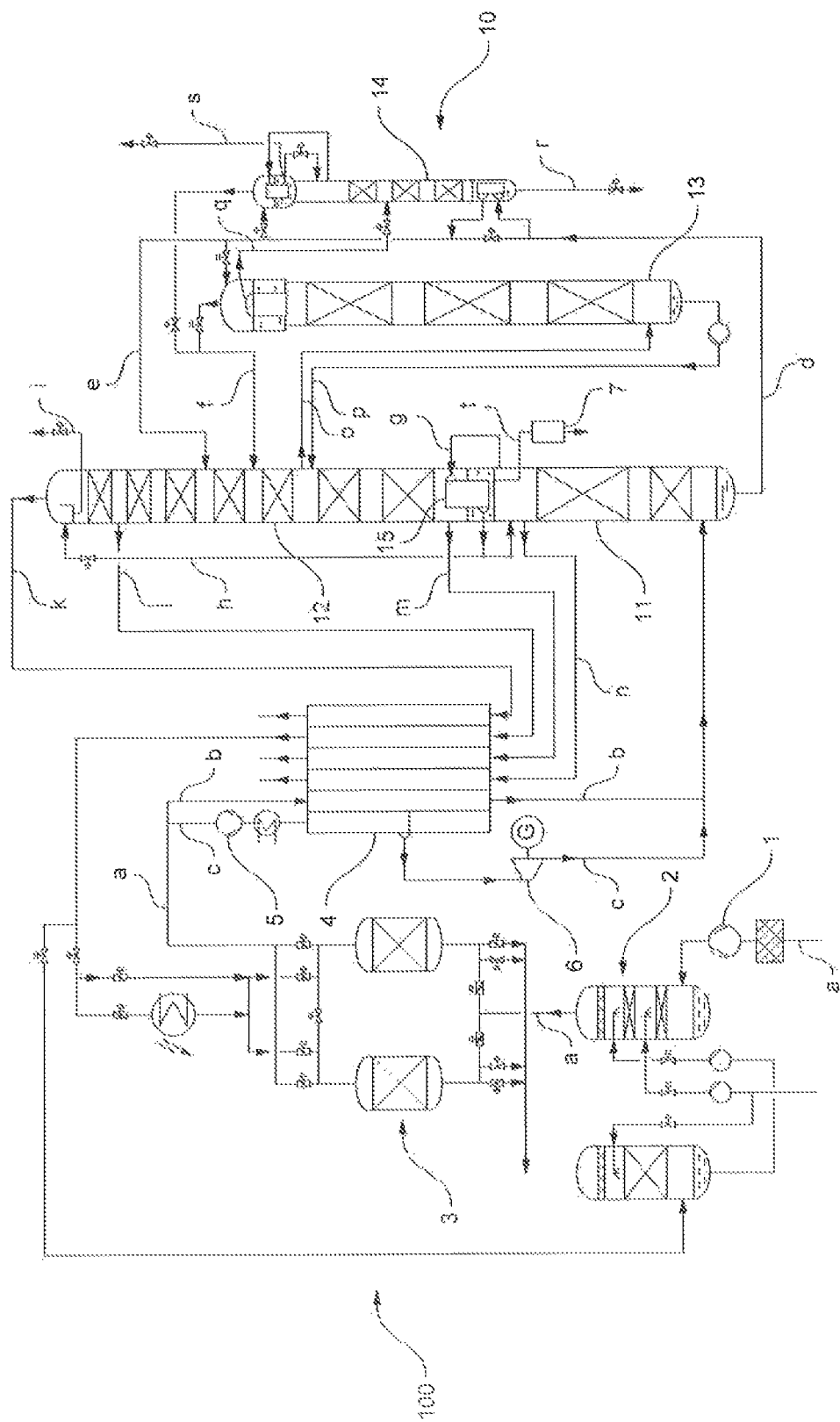

METHOD FOR THE CRYOGENIC FRACTIONATION OF AIR AND AIR FRACTIONATION PLANT

FIELD OF THE INVENTION

The present invention relates to a method for the cryogenic fractionation of air and to a corresponding air fractionation plant.

BACKGROUND OF THE INVENTION

The production of air products in a liquid or gaseous state by the cryogenic fractionation of air in air fractionation plants is known and described, for example, in H.-W. Häring (ed.), Industrial Gases Processing, Wiley-VCH, 2006, in particular section 2.2.5, "Cryogenic Rectification".

Air fractionation plants have distillation column systems which may for example take the form of two-column systems, in particular of conventional Linde double-column systems, but also of three- or multi-column systems. In addition to the distillation columns for obtaining nitrogen and/or oxygen in a liquid and/or gaseous state (for example liquid oxygen (LOX), gaseous oxygen (GOX), liquid nitrogen (LIN) and/or gaseous nitrogen (GAN)), i.e. the distillation columns for nitrogen-oxygen separation, distillation columns may be provided for obtaining further air components, in particular the noble gases krypton, xenon and/or argon.

The present invention is in particular intended for use in air fractionation plants, in which oxygen-rich streams are withdrawn from the distillation column system for nitrogen-oxygen separation predominantly or exclusively in a gaseous state. The invention may, however, also be used in air fractionation plants in which liquid streams are withdrawn from the distillation column system to provide oxygen-rich products, for example in air fractionation plants with internal compression, providing that enrichment of components which are higher-boiling than oxygen as explained below is possible. Air fractionation plants with internal compression are explained for example in loc. cit., section 2.2.5.2, "Internal Compression".

The distillation column systems of typical air fractionation plants are operated at various operating pressures in their distillation columns. Known double-column systems have, for example, a "high-pressure" column (also simply designated pressure column) and a "low-pressure" column. The operating pressure of the high-pressure column amounts for example to 4.3 to 6.9 bar, preferably approx. 5.0 bar. The low-pressure column is operated at an operating pressure of for example 1.3 to 1.7 bar, preferably approx. 1.5 bar, The purpose of having an operating pressure of the low-pressure column which is slightly above atmospheric is essentially to be able to withdraw products from a corresponding air fractionation plant without using additional pumps. The pressures stated here and hereinafter are absolute pressures.

As is known, the air fed into the high-pressure column of a double-column system is used to obtain an oxygen-enriched bottom product (also designated enriched liquid) which is transferred into the low-pressure column. In the low-pressure column, a bottom product predominantly containing oxygen is separated from the oxygen-enriched bottom product from the high-pressure column and optionally further streams fed into the low-pressure column. In order to provide an ascending gas stream in the low-pressure column and so maintain rectification, the bottom product of the low-pressure column is continuously heated, such that a proportion of the bottom product is continuously passing into the gas phase. Heating may proceed in an internal or external condenser-vaporizer, also designated main condenser, which is heated with a gaseous, nitrogen-rich top product from the high-pressure column.

It may here be problematic that, during the described operation of the low-pressure column, less readily volatile components originating from the oxygen-enriched bottom product from the high-pressure column and thus ultimately from the fed air and any further streams fed into the low-pressure column may overtime be enriched in the bottom thereof or in a vaporization chamber of a corresponding external condenser-vaporizer. Components which may be considered critical in this connection are in particular hydrocarbons with up to four carbon atoms, as well as compounds such as nitrous oxide and carbon dioxide, which cannot be completely separated from the feed air using ordinary effort.

Maximum admissible concentrations of corresponding compounds are stated, for Example, in document 65/13/E from the Industrial Gas Council (IGC) of the European Industrial Gases Association (EIGA), Appendices E and F, "Maximum contaminant levels in liquid oxygen thermosyphon reboiler operation at 1.2 bar abs" and "Maximum contaminant levels in liquid oxygen downflow reboiler operation at 1.2 bar abs". As is further explained therein in section 7.3.2, "Purging", the problem of enrichment is less pronounced in plants in which a significant proportion of liquid or gaseous, internally compressed oxygen-rich products is obtained, because in this ease a proportion of the bottom product is continuously drawn off in liquid form from the bottom of the low-pressure column or a vaporization chamber of a corresponding external condenser-vaporizer. However, in air fractionation plants in which only already gaseous, oxygen-rich streams are withdrawn from the low-pressure column, it is in contrast necessary, preferably continuously, to draw off a small proportion of the bottom product as a "scavenging volume". The cited EIGA publication here proposes 0.1 to 0.2% of the introduced air volume. If continuous withdrawal off is not possible, a suitable volume should be withdrawn intermittently, i.e. at least every 12 hours.

Corresponding enrichment of unwanted components may also occur in the top condensers of known air fractionation plants with distillation columns for obtaining argon, the vaporization chamber of which is charged with an oxygen-enriched bottom product from the high-pressure column. The same also applies to the bottoms of krypton/xenon enrichment columns, as explained below. In general corresponding problems occur whenever a liquid volume is fed in a vaporization chamber by means of a cryogenic oxygen-rich liquid and a proportion of the liquid volume is continuously transferred into the gas phase by vaporization, in particular when no appreciable proportions are withdrawn from the liquid volume in liquid form.

In practice, difficulties may arise in adjusting the volume, i.e. the scavenging volume, which is drawn off in liquid form from corresponding vaporization chambers, it is accordingly desirable for economic reasons to keep this volume as small as possible, since it can then typically be put to no further use and is therefore lost from the process. Furthermore, refrigeration losses inevitably occur when cryogenic liquids are discharged without passing through heat exchangers. On the other hand, if the volume is too small the mentioned components are excessively enriched in the vaporization chambers.

There is therefore a requirement tor a simple and reliable way of ascertaining the enrichment of components which are higher-boiling than oxygen in an oxygen-rich, cryogenic liquid, such that a simple and inexpensive way is available which permits verification of compliance with specifications for and/or adjustment of volumes to be withdrawn in this manner.

SUMMARY OF THE INVENTION

This object is achieved by a method for the cryogenic fractionation of air in which a liquid volume present in a vaporization chamber in a distillation column system of an air fractionation plant is fed by means of a cryogenic liquid. A proportion of the liquid volume is continuously transferred into the gas phase by vaporization, wherein, in addition to oxygen, the cryogenic liquid contains components, including xenon, which are higher-boiling than oxygen. According to the invention, the content of xenon in the liquid volume is determined and then used as a measure of an enrichment of the components which are higher-boiling than oxygen in the liquid volume. By this method the content of at least one of the components which are higher-boiling than oxygen can be determined, Using the measurement of enrichment obtained by the inventive method, a flow rate of at least one stream withdrawn in liquid form from the liquid volume can also be ascertained.

The air fractionation plant includes a distillation column system that comprises a high-pressure column and a low-pressure column. The vaporization chamber having the liquid volume of which the content of xenon is determined, is a vaporization chamber of a main condenser which provides a heat-exchanging connection between the high-pressure column and the low-pressure column.

Alternatively, the air fractionation plant may include a crude or pure argon column and the vaporization chamber having the liquid volume of which the content of xenon is determined, is a vaporization chamber of a top condenser of the crude or pure argon column. The cryogenic liquid may be formed from a fluid which is drawn off in liquid form from the high-pressure column and then transferred into the vaporization chamber.

In another embodiment, the fractionation plant with a distillation column system includes a krypton/xenon enrichment column and the vaporization chamber having the liquid volume of which the content of xenon is determined, is the bottom of the krypton/xenon enrichment column The content of at least one hydrocarbon in the vaporization chamber may be determined and its relation to the content of xenon may be used as a measure of a purity of the air fractionated in the air fractionation plant. Alternatively, the content of carbon dioxide or nitrous oxide in the vaporization chamber may be determined, and the relation to the content of xenon may be used for ascertaining the functionality of at least one air purification device of the air fractionation plant.

The proportion of the liquid volume corresponding to 0.1 to 1 percent by volume of the air used to obtain the cryogenic liquid is continuously or intermittently drawn off from the vaporization chamber. The proportion of the liquid volume which is continuously or periodically drawn off from the vaporization chamber is then adjusted on the basis of the content of xenon. The content of xenon may be determined by means of gas chromatography, in particular using a conductivity detector.

The invention also relates to an air fractionation plant configured for the cryogenic fractionation of air in a distillation column system, that includes means configured for feeding a liquid volume present in a vaporization chamber of the distillation column system by means of a cryogenic liquid and for continuously transferring a proportion of the liquid volume into the gas phase by vaporization. In addition to oxygen, the cryogenic liquid contains components, including xenon, which are higher-boiling than oxygen and the plant includes means configured to determine a content of xenon in the liquid volume and to use it as a measure of an enrichment of the components which are higher-boiling than oxygen in the liquid volume.

Before explaining the features and advantages of the present invention, the fundamental principles and terminology used will be explained.

In the language used here, liquid and gaseous streams may be rich or poor in one or more components, wherein "rich" may denote a content of at least 50%, 75%, 90%, 95%, 99%, 99.5%, 99.9% or 99.99% and "poor" a content of at most 50%, 25%, 10%, 5%, 1%, 0.1% or 0.01% on a molar, weight or volume basis. The term "predominantly" may correspond to the definition of "rich". In the language used here, liquid and gaseous streams may furthermore be enriched or depleted in one or snore components, wherein these terms relate in the case of air fractionation to introduced air or the constituents thereof. The liquid or gaseous stream is "enriched" if it contains at least 1.1 times, 1.5 times, 2 times, 5 times, 10 times, 100 times or 1,000 times the content and "depleted" if it contains at most 0.9 times, 0.5 times, 0.1 times, 0.01 times or 0.001 times the content of a corresponding component, relative to the respective content in the introduced air. If "liquid oxygen" is mentioned here, it should be taken to mean a liquid stream which is rich in oxygen, but need not exclusively consist of oxygen.

Cryogenic liquids are obtained at various points in air fractionation plants and continuously vaporized in vaporization chambers while maintaining specified filling levels. This is for example the case in the above-explained bottom of the low-pressure column which simultaneously constitutes a vaporization chamber of a main condenser. A corresponding main condenser may, of course, also be arranged outside a double-column system, it which case it is designated an external main condenser. The present invention is applied in any desired vaporization chambers, in particular in vaporization chambers of condenser-vaporizers. It is characteristic of a vaporization chamber that a liquid volume is formed and maintained therein by means of a cryogenic liquid, a proportion of which liquid volume is continuously transferred into the gas phase by vaporization. A "condenser-vaporizer" has a liquefaction chamber and a vaporization chamber. Vaporization and liquefaction chambers are in each case formed of groups of passages (liquefaction or vaporization passages) which are in fluidic connection with one another. In the liquefaction chamber condensation of a first fluid stream is carried out, with vaporization of a second fluid stream taking place in the vaporization chamber. The two fluid streams are here in indirect heat exchange.

A "cryogenic" liquid, or a corresponding fluid, liquid air product stream etc, is taken to mean a liquid medium, the boiling point of which is distinctly below the respective ambient temperature, for example less than 200 K, in particular 77 K to 110 K. Examples of cryogenic media are liquid air, liquid oxygen and liquid nitrogen as defined above.

The method and plant of the invention provide a number of advantages. The present invention proceeds from a per se known method for the cryogenic fractionation of air, in which a liquid volume present in a vaporization chamber in a distillation column system of an air fractionation plant is fed by means of a cryogenic liquid and in which a proportion of the liquid volume is continuously transferred into the gas phase by vaporization. In addition to oxygen, the cryogenic liquid, in particular an oxygen-enriched liquid from the bottom of a low-pressure column, contains components, including xenon, which are higher-boiling than oxygen. In particular, in the context of the above-stated definition, a corresponding liquid may predominantly consist of oxygen. Components which are higher-boiling than oxygen may, of course, also be present. The content of xenon is determined by the xenon content of the natural air, which is substantially constant around the globe. Xenon is not retained by conventional, purification devices for feed air in air fractionation plants and causes no further disruption to the separation.

On the other hand, the content of the at least one further component which is higher-boiling than oxygen is determined inter alia by the location at which a corresponding air fractionation plant is operated. As stated in the above-cited EIGA document, in particular section 7.4, "Contaminant Analysis", an elevated content of such components is to be expected in particular in highly industrialized regions with chemical, petrochemical and metallurgical plants. Depending on the nature of the industry, elevated quantities of nitrous oxide, hydrocarbons and/or carbon dioxide may be observed. While carbon dioxide in particular is largely removed in conventional feed air purification devices, residual contents may be fed into a corresponding distillation column system.

The present invention proposes determining the content of xenon in the liquid volume and to use it as a measure of any enrichment of the components which are higher-boiling than oxygen in the liquid volume.

The invention may here involve using xenon as a measure of a concentration of at least one of the components which are higher-boiling than oxygen in a corresponding liquid volume. On the basis of the content of xenon determined in the liquid volume, it is thus possible to determine a content of at least one of the components which are higher-boiling than oxygen. As is also explained below, this has the advantage that it is only necessary to determine the content of one component, namely xenon, and the concentration of one or more components may be estimated at least to an order of magnitude on this basis. Measuring other, in particular a plurality of different, components which are higher-boiling than oxygen, optionally using different analyzers, is in this case no longer necessary.

The invention is, however, also in particular advantageous in eases in which just the enrichment itself is ascertained. Plow-measuring devices are accordingly not necessarily provided in the vaporization chambers in question here, for example in a bottom of a low-pressure column or a vaporization chamber of a top condenser of a crude argon column (see below), because it is extremely complex to measure small streams of cryogenic liquids. By virtue of their design, ultrasound probes which are typically used have slots which are undesirable in particular in the region of highly enriched oxygen because it is precisely there that enrichment of hydrocarbons might occur. The scavenging volumes withdrawn from these vaporization chambers are therefore conventionally frequently comparatively roughly estimated from the valve size used and the withdrawal time or the frequency of withdrawal. Using xenon as a measure of the enrichment of the components which are higher-boiling than oxygen, as proposed according to the invention, considerably facilitates the determination of the correct scavenging volume. It may be sufficient for the purposes of the present invention to increase the scavenging volume appropriately in the event of excessive enrichment and to confirm the result on the basis of a further measurement.

It may thus also be provided for the purposes of the present invention to ascertain, on the basis of the measure of enrichment, a flow rate of at least one stream withdrawn in liquid form from the liquid volume. Such a flow rate is thus ascertained indirectly, such that it is possible to dispense with the use of complex flow-measuring devices.

Using xenon has proven particularly advantageous for the purposes of the present invention because, as mentioned, xenon occurs at a substantially constant concentration in outdoor air. Xenon is furthermore so sparingly volatile that when other components, in particular oxygen, vaporize from the liquid volume it substantially remains therein, i.e. it does not pass over or at most passes over only slightly into the gas phase. The latter is in particular not the case with other components theoretically likewise usable as markers or indicators such as krypton and argon.

If, in a corresponding liquid volume, for example in the case of exclusively gaseous oxygen products being withdrawn from a low-pressure column, a typical enrichment factor of 500 is assumed, the minimum xenon concentration in the liquid volume is 500 times the concentration in air, thus 500×0.086 vppm and hence 43 vppm. Such a concentration is comparatively simply measurable using known measurement devices, as explained below.

Thus, if a content of 43 vppm of xenon is measured in a liquid volume of a corresponding vaporization chamber in the explained example, it may conversely be assumed that xenon has been enriched 500 times in the vaporization chamber, so the scavenging volume thus amounted to 1/500 of the introduced air volume. The invention thus permits reliable determination of enrichment without entailing flow measurement which, in particular at cryogenic temperatures, is complex.

Since the content of xenon in ambient air is known and the contents of other components which are higher-boiling than oxygen, such as nitrous oxide and carbon dioxide, may be sufficiently reliably estimated to an order of magnitude, it is possible, on the basis of the xenon content in the liquid volume, to draw conclusions as to the content of the further components which are higher-boiling than oxygen.

A determination to an order of magnitude may here be sufficient. If, for example, a value of approx, 2 vppm of methane or approx. 0.32 vppm of nitrous oxide is assumed in the introduced air, which is correct in the large majority of cases, and the determined content of xenon in the liquid volume reveals a 1,000 times enrichment, the maximum value for methane will be 2,000 vppm, provided that no methane vaporizes from the liquid volume. This is the ease for example in arrangements with "barrier" plates, as are used when obtaining krypton and xenon. If ⅓ of the methane passes over into the gas phase, the actual content in the liquid volume is in contrast only 1,300 vppm. In the case of a maximum admissible concentration of 500 vppm of methane this means in any event that too much methane is present. The same possibly also applies to other troublesome air components. Separate measurement of methane and other troublesome air components such as nitrous oxide and carbon dioxide is, however, not required.

EP 0 726 434 B1 proposed using nitrous oxide as a marker. Nitrous oxide is, however, to be considered critical in relatively large quantities in corresponding liquid volumes because at low temperatures it may form mixed crystals with carbon dioxide which are capable of blocking passages in the heat exchangers. As a result, this may lead to an elevated pressure drop and indirect enrichment of hydrocarbons in regions of low flow.

The particular advantage of using xenon, as is proposed according to the invention, is, as has already in part been mentioned, that xenon is not retained by either molecular sieve or liquid adsorbers, i.e. typical purification devices used in air fractionation plants. Xenon, which is present in the Introduced air in comparatively simply detectable concentrations, thus passes over in its entirety into a corresponding liquid volume. Xenon is moreover sufficiently heavy to remain completely in the liquid volume, i.e. there is, for example, no discharge via a gaseous oxygen product. No other component which is naturally present in a corresponding liquid volume of an air fractionation plant has these characteristics.

The method according to the invention provides particular advantages in an air fractionation plant, as has been explained above, namely an air fractionation plant with a distillation column system which comprises a high-pressure column and a low-pressure column. In this case, the liquid volume is vaporized in a vaporization chamber of a condenser-vaporizer, the explained main condenser, which provides a heat-exchanging connection between the high-pressure column and the low-pressure column, This liquid volume is fed with oxygen-enriched liquid from the high-pressure column. The invention is particularly advantageous if a corresponding air fractionation plant is not configured for internal compression of oxygen, i.e. if the oxygen of the low-pressure column is only withdrawn in the form of one or more oxygen-enriched gaseous streams.

The present invention is, however, also particularly suitable for air fractionation plants with columns for obtaining argon, accordingly for example for air fractionation plants which comprise a crude argon column, In this case, the liquid volume is vaporized in a vaporization chamber of the top condenser of the crude argon column, fn order to prevent undesirably high concentrations of troublesome components being enriched in corresponding liquid volumes, a proportion thereof is typically drawn off via a line and continuously transferred into the low-pressure column. Since, however, for the explained reasons, this typically does not proceed with flow monitoring, excessive enrichment of unwanted components may occur for example in the case of (even partial) blockage of a corresponding line. This may be identified thanks to the determination of xenon content according to the invention and prevented by implementing suitable measures. Correspondingly, the present Invention is, however, also suitable for the determination of components which are higher-boiling than oxygen in top condensers of pure argon columns or for any other desired additional vaporization chambers in corresponding condensers or other vaporization devices. In all cases, the liquid volume is advantageously Conned from a fluid which is drawn off in liquid form from the high-pressure column and transferred into the corresponding vaporization chamber.

Particular advantages are, however, also achieved for the purposes of the present invention if the content of xenon is determined in the bottom of a krypton/xenon enrichment column as vaporization chamber. Corresponding enrichment columns are known from the relevant specialist literature, for example H.-W. Häring (ed.), Industrial Gases Processing, Wiley-VCH, 2006, in particular section 3.3, "Recovery of Krypton and Xenon". They are typically fed from the bottom of the low-pressure column, thus in turn from a liquid volume of a vaporization chamber.

Krypton and xenon are typically enriched by a factor of 2,000 to 3,000 in the bottom of an enrichment column. Determining the content of xenon at this point provides information not only about the quality of the product which is to be further processed (i.e. the actual enrichment factor), but also about the methane contamination of the outdoor air. Methane is not retained by molecular sieve adsorbers. If, therefore, the xenon content in the bottom of the enrichment column is low (tor example 43 vppm, which, as mentioned, would suggest 500 times enrichment), but the concentration of hydrocarbons is unexpectedly high, the outdoor air concentration of is out-of-specification, i.e. an unusually high level of air pollution is present. The content of hydrocarbons is known in this specific case because the enrichment column is operated on the basis of the total hydrocarbon content, which is suitably monitored for this purpose.

The contents of nitrous oxide and carbon dioxide in the bottom of the enrichment column are also typically monitored. If excessively high concentrations of carbon dioxide (above 2 vppm) and/or nitrous oxide (above 50 vppm) occur and the xenon concentration is simultaneously in the normal range, it may be assumed that the molecular sieve adsorber is malfunctioning. For example, an unwanted air bypass may be present. Such malfunctioning is distinctly more difficult to identify at another point within the air fractionation plant.

In brief, the present invention thus advantageously provides determining a content of at least one hydrocarbon in the vaporization chamber, relating it to the content of xenon and using it as a measure of a purity of the air fractionated in the air fractionation plant and/or determining a content of carbon dioxide and/or nitrous oxide in the vaporization chamber, relating it to the content of xenon and using it to ascertain the functionality of at least one air purification device of the air fractionation plant, in this manner, determining the content of xenon in the bottom of the enrichment column thus permits indirect monitoring of the outdoor air concentration for elevated hydrocarbon contamination and simultaneous monitoring of the operation of the molecular sieve adsorber.

As explained above, a proportion of the liquid volume amounting to 0.1 to 1 percent by volume of the air used to obtain the cryogenic liquid is advantageously drawn off continuously or periodically from corresponding vaporization chambers. In this manner, excessive enrichment of corresponding components may be reliably prevented.

The invention is particularly advantageous if the proportion of the liquid volume which is continuously or periodically drawn off from the vaporization chamber is adjusted on the basis of the content of xenon which, as mentioned, is used as a measure of a content of the at least one further component which is higher-boiling than oxygen in the cryogenic liquid. The present invention may here be implemented in the context of a control method which automatically controls the proportion to be drawn off for example on the basis of the content of xenon.

Gas chromatography is in particular suitable for determining the xenon content in the above-explained concentration, in particular if a thermal conductivity detector (TCD) is used for this purpose. Corresponding chromatographic methods are simple, robust and inexpensive to carry out.

The present invention may be implemented either in an air fractionation plant or by means of a separate measurement device provided separately from the air fractionation plant. For example, the content of xenon may be measured using a periodically measuring measurement device of the air fractionation plant or the content of xenon may be measured by withdrawing a measurement sample from the vaporization chamber and transferring it to the measurement device in a sample container. Suitable sample containers are for example sample cylinders or plastics-coated metal foil pouches specifically designed for transporting gases. There is thus no need to make a measurement in situ.

The present invention also provides an air fractionation plant which is configured for the cryogenic fractionation of air in a distillation column system. Such an air fractionation plant comprises means which are configured for feeding a liquid volume present in a vaporization chamber in the distillation column system by means of a cryogenic liquid and continuously transferring a proportion of the liquid volume into the gas phase by vaporization, wherein, in addition to oxygen, the cryogenic liquid contains components, including xenon, which are higher-boiling than oxygen. According to the invention, means are provided winch are configured for determining a content of xenon in the liquid volume and using it as a measure of any enrichment of the components which are higher-boiling than oxygen in the liquid volume.

Such an air fractionation plant, for the features and advantages of which reference is explicitly made to the above-explained features and advantages, is in particular configured for carrying out a method as has previously been explained, and has the corresponding means.

The invention is explained in greater detail below with reference to the attached drawing which shows an air fractionation plant, on the basis of which the measures according to the invention are explained.

BRIEF DESCRIPTION OF THE DRAWINGS

FIG. 1 shows an air fractionation plant in the form of a schematic process flow chart.

DETAILED DESCRIPTION OF THE INVENTION

FIG. 1 shows an air fractionation plant, on the basis of which one embodiment of the invention is illustrated. The air fractionation plant is designated overall as 100.

In the air fractionation plant 100, a feed air stream a is drawn in via a filter (without reference sign) and compressed by means of a main air compressor 1. The correspondingly compressed feed air stream a is supplied to a precooling device 2 which is operated with cooling water and is not explained in greater detail here. The precooled feed air stream, still designated a, is purified in a purification device 3. In the purification device 3, which typically comprises a pair of alternately operated adsorber containers (molecular sieve adsorbers), the precooled feed air stream has water and carbon dioxide largely but, due to the underlying principle, incompletely removed from it.

Downstream from the purification device 3, the feed air stream, here still designated a, is divided into two sub-streams b and c. Sub-stream b is cooled at the pressure level of feed air stream a in a main heat exchanger 4. Sub-stream c is post-compressed in a post-compressor 5 and likewise cooled in the main heat exchanger 4, but only to an intermediate temperature level. After cooling to the intermediate temperature level, this sub-stream c, or "turbine stream", is here expanded by means of a generator turbine 6 to the pressure level of sub-stream b, combined with the latter and fed into a high-pressure column 11 of a distillation column system 10 explained below in detail.

In the high-pressure column 11 of the distillation column system 10, an oxygen-enriched liquid bottom fraction and a nitrogen-enriched gaseous top fraction are formed from the feed air fed in via sub-streams b and c. The oxygen-enriched liquid bottom fraction is drawn off as stream d from the high-pressure column 11, in part used as a heating medium in a bottom vaporizer of a pure argon column 14 (see below) and in each case fed in defined proportions into a top condenser of the pure argon column 14, a top condenser of a crude argon column 13 and, as stream e, into a low-pressure column 12 of the distillation column system 10. Fluid vaporizing in the vaporization chambers of the top condensers of the crude argon column 13 and the pure argon column 34 is likewise transferred, as stream f, into the low-pressure column 12.

The gaseous nitrogen-rich top product in the form of stream g may be drawn off front the top of the high-pressure column 11, liquefied in a main condenser 15, which creates a heat-exchanging connection between the high-pressure column 11 and the low-pressure column 12, and charged in portions as a return to the high-pressure column 11 and expanded in the low-pressure column 12.

A liquid nitrogen-rich stream i may be drawn off from a liquid retention device at the top of the low-pressure column 12 and exported from the air fractionation plant 100 as a liquid nitrogen product. A gaseous nitrogen-rich stream k drawn off from the top of the low-pressure column 12 is passed through the main heat exchanger 4 and provided as a nitrogen product at the pressure of the low-pressure column. A stream 1 is furthermore drawn off from an upper region of the low-pressure column 12 and, after heating in the main heat exchanger 4, is used as "impure" nitrogen in the preheating device 2 or, after heating by means of an electrical heater, is used in the purification unit 3.

An oxygen-rich gaseous stream m is drawn off from a lower region of the low-pressure column 12 and, likewise after heating in the main heat exchanger 4, provided as a corresponding oxygen product. A nitrogen-rich stream n is withdrawn from an upper region of the high-pressure column 11, is heated in the main heat exchanger 4 and provided as a gaseous compressed nitrogen product at the pressure of the high-pressure column 11.

It will be noted that while liquid is indeed condensed in the bottom zone of the low-pressure column 12 in the air fractionation plant 100, as illustrated in FIG. 1, no liquid is normally withdrawn from the liquid volume present in this vaporization chamber. Since, in the air fractionation plant 100 shown, oxygen is merely withdrawn from a lower region of the low-pressure column 12 in the form of the gaseous stream m, but not, as in known internal compression methods, liquid oxygen, enrichment of components which are higher-boiling than oxygen may therefore occur in the bottom of the low-pressure column.

In order to obtain pure argon, a stream o is withdrawn from the low-pressure column 12 at the known argon transition or just below and transferred into the already mentioned crude argon column 13. A condensate arising in the bottom of the crude argon column 13 is pumped back into the low-pressure column 12 in the form of stream p. At the top of crude argon column 13, fluid which does not condense out in the top condenser is drawn off in the form of stream q and transferred into the pure argon column 14. In the pure argon column 34, liquid argon r is obtained using the already mentioned bottom vaporizer and the likewise mentioned top condenser. A certain proportion leaves the pure argon column as stream s and is blown off into the atmosphere.

It will be noted that while fluids do indeed arise in the top condensers of the crude argon column 13 and the pure argon column 14, in a similar way as in the bottom of the low-pressure column 12, or liquid streams are fed in here, no liquid streams are withdrawn. The above-mentioned enrichment of higher-boiling components may therefore occur here too. FIG. 1 does not illustrate any withdrawal of fluid, as is typically provided, for preventing corresponding enrichment.

The present invention therefore for example proposes, as has already repeatedly been explained, examining liquid volumes present in corresponding vaporization chambers, which are in particular taken to mean the vaporization chambers in the bottom of the low-pressure column 12, in the top condenser of the crude argon column 13 and in the top condenser of the pure argon column 14, for their xenon contents and, in the event, of a specified value being exceeded, implementing appropriate measures.

In the example shown, a stream t and a device 7 are illustrated for this purpose. Stream t is a proportion intermittently withdrawn from the liquid volume in the vaporization chamber of the low-pressure column, which proportion is examined for its xenon content in the device 7. As has repeatedly been explained, examination may proceed, for example, by means of gas chromatography. Examination need not proceed in situ, i.e. in the air fractionation plant 100 itself, but it may also be provided to examine the proportion withdrawn from the vaporization chamber of the low-pressure column for its xenon content in an external device.

It will be understood that the embodiments described herein are merely exemplary and that one skilled in the art may make variations and modifications without departing from the spirit and scope of the present invention. All such variations and modifications are intended to be included within the scope of the invention as described above. Further, all embodiments disclosed are not necessarily in the alternative, as various embodiments of the invention may be combined to provide the desired result.

The invention claimed is:

1. A method for cryogenic fractionation of air, said method comprising:
   fractionating air in a distillation column system of an air fractionation plant to obtain a cryogenic liquid containing oxygen;
   feeding said cryogenic liquid containing oxygen into a liquid volume present in a vaporization chamber in said distillation column system of said air fractionation plant, and
   continuously transferring a proportion of the liquid volume into the gas phase by vaporization, wherein, in addition to oxygen, said cryogenic liquid contains xenon and at least one further component having a boiling point higher than the boiling point of oxygen, and
   determining the content of xenon in the liquid volume and using the determined content of xenon as a measure of the content in the liquid volume of said at least one further component having a boiling point higher than the boiling point of oxygen in the liquid volume.

2. The method according to claim 1, further comprising withdrawing at least one stream withdrawn in liquid form from the liquid volume wherein the flow rate of said at least one stream is selected based on the determination of the content of xenon.

3. The method according to claim 1, wherein said distillation column system comprises a high-pressure column and a low-pressure column.

4. The method according to claim 3, in which said vaporization chamber is a vaporization chamber of a main condenser which provides a heat-exchanging connection between the high-pressure column and the low-pressure column.

5. The method according to claim 3, wherein said distillation column system further comprises a crude argon column and said vaporization chamber is a vaporization chamber of a top condenser of the crude argon column.

6. The method according to claim 3, wherein said distillation column system further comprises a pure argon column and said vaporization chamber is a vaporization chamber of a top condenser of the pure argon column.

7. The method according to claim 3, in which the cryogenic liquid is formed from a fluid which is drawn off in liquid form from the high-pressure column and then transferred into the vaporization chamber.

8. The method according to claim 1, wherein said distillation column system comprises a krypton/xenon enrichment column, and said vaporization chamber is the bottom of the krypton/xenon enrichment column.

9. The method according to claim 8, wherein said at least one further component having a boiling point higher than the boiling point of oxygen whose content in the liquid volume is measured based on the content of xenon is at least one hydrocarbon and the measured content of said at least one hydrocarbon is used as a measure of a purity of the air fractionated in the air fractionation plant.

10. The method according to claim 8, wherein said at least one further component having a boiling point higher than the boiling point of oxygen whose content in the liquid volume is measured based on the content of xenon is carbon dioxide and/or nitrous oxide and the measured content of carbon dioxide and/or nitrous oxide is used for ascertaining the functionality of at least one air purification device of the air fractionation plant.

11. The method according to claim 1, in which a proportion of the liquid volume corresponding to 0.1 to 1 percent by volume of the air used to obtain the cryogenic liquid is continuously or intermittently drawn off from the vaporization chamber.

12. The method according to claim 11, in which the proportion of the liquid volume which is continuously or periodically drawn off from the vaporization chamber is adjusted on the basis of the content of xenon.

13. The method according to claim 1, in which the content of xenon is determined by means of gas chromatography.

14. The method according to claim 13, in which the content of xenon is determined by using a conductivity detector.

15. The method according to claim 4, wherein said cryogenic liquid is formed from a fluid withdrawn in liquid form from the high-pressure column and then transferred into said vaporization chamber.

16. The method according to claim 1, wherein said at least one further component having a boiling point higher than the boiling point of oxygen in the liquid volume is nitrous oxide, carbon dioxide or at least one hydrocarbon.

17. The method according to claim 1, further comprising withdrawing at least one stream withdrawn in liquid form from the liquid volume and adjusting the amount of said at least one stream withdrawn on the basis of the determination of the content of xenon.

18. The method according to claim 4, wherein said main condenser is arranged outside of the high-pressure column and the low-pressure column.

19. A method for cryogenic fractionation of air, said method comprising:

fractionating air in a distillation column system of an air fractionation plant to obtain a cryogenic liquid containing oxygen;

feeding said cryogenic liquid containing oxygen into a liquid volume present in a vaporization chamber in said distillation column system of said air fractionation plant, and continuously transferring a proportion of the liquid volume into the gas phase by vaporization, wherein, in addition to oxygen, said cryogenic liquid contains xenon and at least one further component having a boiling point higher than the boiling point of oxygen, and determining the content of xenon in the liquid volume and using the determined content of xenon to determine the amount of enrichment in the liquid volume of at least one further component having a boiling point higher than the boiling point of oxygen in the liquid volume, in comparison to the amount of said at least one further component in the air fed to said distillation column system.

\* \* \* \* \*